(12) United States Patent
Bhavani

(10) Patent No.: US 9,928,343 B2
(45) Date of Patent: Mar. 27, 2018

(54) TAG BASED KNOWLEDGE SYSTEM FOR HEALTHCARE ENTERPRISES

(75) Inventor: Neeraj Bhavani, Aliso Viejo, CA (US)

(73) Assignee: TAGNOS, INC., Irvine, CA (US)

( * ) Notice: Subject to any disclaimer, the term of this patent is extended or adjusted under 35 U.S.C. 154(b) by 241 days.

(21) Appl. No.: 11/733,056

(22) Filed: Apr. 9, 2007

(65) Prior Publication Data
US 2009/0106692 A1 Apr. 23, 2009

Related U.S. Application Data

(60) Provisional application No. 60/791,058, filed on Apr. 10, 2006, provisional application No. 60/822,737, filed on Aug. 17, 2006.

(51) Int. Cl.
G06F 19/00 (2018.01)
(52) U.S. Cl.
CPC .................. G06F 19/327 (2013.01)
(58) Field of Classification Search
CPC .... G06Q 50/22; A61B 5/1113; G06F 19/3418
USPC ......................................................... 705/2–3
See application file for complete search history.

(56) References Cited

U.S. PATENT DOCUMENTS

| | | | |
|---|---|---|---|
| 6,466,125 B1 | 10/2002 | Richards et al. | |
| 6,970,097 B2 * | 11/2005 | Welles, II | G01S 1/725 340/539.13 |
| 7,333,002 B2 * | 2/2008 | Bixler | G06Q 10/087 340/10.1 |
| 7,382,247 B2 * | 6/2008 | Welch | A61B 5/0024 340/539.1 |
| 7,480,629 B2 | 1/2009 | Dashefsky et al. | |
| 2003/0074222 A1 * | 4/2003 | Rosow | G06Q 10/02 705/2 |
| 2004/0064037 A1 * | 4/2004 | Smith | G06T 7/0012 600/420 |
| 2004/0204963 A1 | 10/2004 | Klueh et al. | |
| 2005/0021369 A1 * | 1/2005 | Cohen | G06F 19/327 705/2 |

(Continued)

OTHER PUBLICATIONS

Vogt, Multiple Object Identification with Passive RFID Tags, Oct. 2002, IEEE International Conference on Systems, Man and Cybernetics, pp. 4-9.*

(Continued)

*Primary Examiner* — Joy Chng
(74) *Attorney, Agent, or Firm* — Fish IP Law, LLP

(57) ABSTRACT

Contemplated systems and methods provide an integration platform to facilitate the exchange of information between RFID tagged objects and non-RFID systems. In especially preferred aspects, RFID tagged objects include patients, personnel, and assets of a healthcare facility, while preferred non-RFID systems include asset management systems, time-keeping systems, electronic medical records systems, and hospital and pharmacy information systems. Contemplated systems and methods will apply rules to associate RFID information with events, which will then be correlated with appropriate steps that can be effected in a varied and automated manner. In further preferred aspects, RFID technology is employed to upgrade patient telemetry to provide positional information the hospital system.

41 Claims, 12 Drawing Sheets

(56) References Cited

U.S. PATENT DOCUMENTS

| | | | |
|---|---|---|---|
| 2005/0027570 A1* | 2/2005 | Maier | G06F 19/321 |
| | | | 705/3 |
| 2005/0035862 A1* | 2/2005 | Wildman | A61B 5/1113 |
| | | | 340/573.1 |
| 2005/0092825 A1* | 5/2005 | Cox, Jr. | G06K 7/0008 |
| | | | 235/375 |
| 2005/0114177 A1* | 5/2005 | Sweeney | G06Q 10/10 |
| | | | 705/2 |
| 2005/0149358 A1 | 7/2005 | Sacco et al. | |
| 2005/0216212 A1 | 9/2005 | Bellin et al. | |
| 2005/0283382 A1* | 12/2005 | Donoghue | G06Q 10/10 |
| | | | 705/2 |
| 2006/0151424 A1 | 7/2006 | Graves et al. | |
| 2006/0178913 A1 | 8/2006 | Lara et al. | |
| 2006/0192655 A1 | 8/2006 | Levin | |
| 2006/0282302 A1 | 12/2006 | Hussain | |
| 2007/0129983 A1* | 6/2007 | Scherpbier | G06Q 50/22 |
| | | | 705/2 |
| 2007/0288263 A1 | 12/2007 | Rodgers | |

OTHER PUBLICATIONS

Vogt, Multiple Object Identification With Passive RFID Tags, Oct. 2002, IEEE International Conference on Systems, Man and Cybernetics, pp. 4-9 (Year: 2002).* www.informationweek.com/news/mobility/RFID/showsArticle. jhtml . . . "Cisco Combines RFID Location Tools with Wi-Fi" May 4, 2005.

* cited by examiner

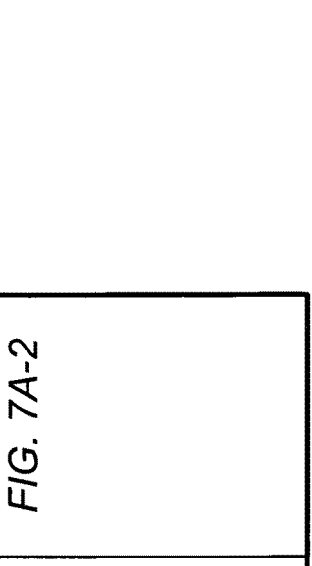
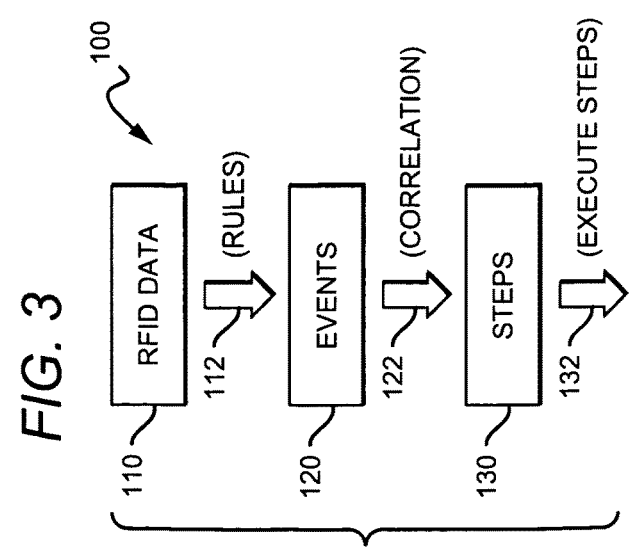

FIG. 4

RFID DATA

| Tag ID | 2342342 | 34534624563 | 23424 | 2354457678 |
|---|---|---|---|---|
| Tag Type | Staff | Equipment | Patient | Staff |
| Tag Name | Dr. Jones | pump #3231 | Bill Peterson | Nurse Betty |
| Coordinates | 222,242 | 888,445 | 228,789 | 114,738 |
| Time Stamp | 1:00 | 1:00 | 12:58 | 1:00 |

FIG. 6

CORRELATION ENGINE TABLE

|  | RECORD 1 | RECORD 2 | RECORD 3 | RECORD 4 |
|---|---|---|---|---|
| Event A | Dr. Jones arriving in ER | Betty Smith ariving at hospital | Bill Peterson, New Patient/ New Room #403 | IV pump #3231 Just Sterilized |
| Event B | IV pump #3231 Just Sterilized | | | |
| Event C | Bill Peterson, New Patient/ New Room #403 | | | |
| Event D | Betty Smith ariving at hospital | | | |
| Event E | | | | |
| | | | | |
| Action A | take IV pump #3231 from sterilization room to room #403 | send message to nurse call system | update bed management system | take IV pump #3231 from sterilization room to storage |
| Action B | | update patient chart | | |
| Action C | | update maintenance schedule | | |
| Action D | | send procedure data to accounting system | | |
| Action E | | | | |
| Action F | | | | |

*FIG. 5*

EVENT RULE TABLE

| | RECORD 1 | RECORD 2 | RECORD 3 | RECORD 4 |
|---|---|---|---|---|
| Name | Dr. Jones arriving in ER | IV Pump | Patient | Betty Smith arriving at hospital got notified to look for IV pump for patient Bill Peterson |
| Conditions | | | | |
| Who | Dr. Jones | pump #3231 | Bill Peterson | Betty Smith |
| How many | 1 | 1 | 1 | 1 |
| What | arriving | in sterilization | changing room | arriving |
| Where | ER zone 1 | sterilizing | ER zone 1 | Security lobby |
| When | 1:10 | 12:30 | 1:05 | 1:15 |
| | | | | |
| Actions | | | | |
| system alert | true | true | true | true |
| email | betty@xyz.org | - | betty@xyz.org | home@xyz.org |
| page | 777-888-9999 | - | 777-888-9999 | 777-888-1234 |
| assign to | Betty Smith | - | Betty Smith | Dr. Jones |
| severity | low | - | low | low |
| message | Dr. Jones in ER | - | Bill Peterson changing room from #206 to #403 | Betty in ER |
| | | | | |
| Escalation | | | | |
| unhandled | 5 min | - | - | - |
| reassign to | name | - | - | - |
| system alert | - | - | - | - |
| email | - | - | - | - |
| page | - | - | - | - |
| | | | | |
| Scheduling | | | | |
| when-now | true | true | true | true |
| when-at | 1:30 | 1:30 | 1:30 | 1:30 |
| when-on | 3/15/06 | 3/15/06 | 3/15/06 | 3/15/06 |
| how often-once | false | false | false | false |
| how often-until | false | false | false | false |
| how often-forever | true | true | true | true |

FIG. 7A-1

TALS COMMAND CENTER

| Tracking | Workflow | System Status | Reports |
| Staff | Patient/Visitor | Medical |

Search Options

Area [Radiology ▼]

☐ People ☑ Entertainment ☐ Supplies

[Search]

| Tag ID |
|---|
| VEN1 |
| BPM1 |
| IVP1 |
| XRY2 |

Refresh Time : Apr 10, 2006 12:50:54

- Refresh Map
- Cyclic View
- Auto Refresh

Map showing: CT, Control Room, CT, Office, Office, MRI, Control Room, MRI, Floursc, XRa, XRa, Office, Kitchen, File Rc Name: _____ Zone: _____

| Alerts | Security | Safety | Asset | Severity | |
|---|---|---|---|---|---|
| Critical | 0 | 0 | 1 | ● | Siemens Servo I Moved |
| Major | 0 | 0 | 2 | ● | Patient Mr. T. Rogio in |
| Minor | 0 | 0 | 1 | ● | Dr. Jones has entered |
| Unacknowledged | 0 | 0 | 4 | ● | Dr. Katti has entered E |

● =Critical  ● =Major  ● =Minor

FIG. 7A-2

| Name | Location | Department |
|---|---|---|
| Ventilator1 | Room 90 | ICU |
| BP Machine 1 | Room 103 | Lab |
| IV Pump 1 | Room 129 | ICU |
| X-Ray 2 | Room 345 | XRay |

Search Results

Powered By TAGNOS

Administration | Support | Network | MAP ONLY
Supplies | Medical Equipment | Location Apr 10, 2006 12:57:40

Reception
US
Workstations
Supply Room
Reading Room | Conference Room
Phone:

| Description | Time | Ack | Ignore | Silence |
|---|---|---|---|---|
| From ICU #3 to #5 | 2:30 AM 11/7/04 | ✓ | ⊘ | ✗ |
| Waiting Room A | 6:10 AM 11/7/04 | ✓ | ⊘ | ✗ |
| CU | 2:30 AM 11/7/04 | ✓ | ⊘ | ✗ |
| R | 5:30 AM 11/7/04 | ✓ | ⊘ | ✗ |

Show All

*FIG. 7B-2*

Powered By TAGNOS

| Administration | Support | Network | MAP ONLY |
| Supplies | Medical Equipment | Location | |

Search Results

| Name | Location | Department |
|---|---|---|
| Ventilator1 | Room 90 | ICU |
| BP Machine 1 | Room 103 | Lab |
| IV Pump 1 | Room 129 | ICU |
| X-Ray 2 | Room 345 | XRay |

Apr 10, 2006 12:57:40

Workstatic

Phone:

| Description | Time | Ack | Ignore | Silence |
|---|---|---|---|---|
| From ICU #3 to #5 | 2:30 AM 11/7/04 | ☑ | ⊘ | 🔇 |
| Waiting Room A | 6:10 AM 11/7/04 | ☑ | ⊘ | 🔇 |
| CU | 2:30 AM 11/7/04 | ☑ | ⊘ | 🔇 |
| | 5:30 AM 11/7/04 | ☑ | ⊘ | 🔇 |

Show All

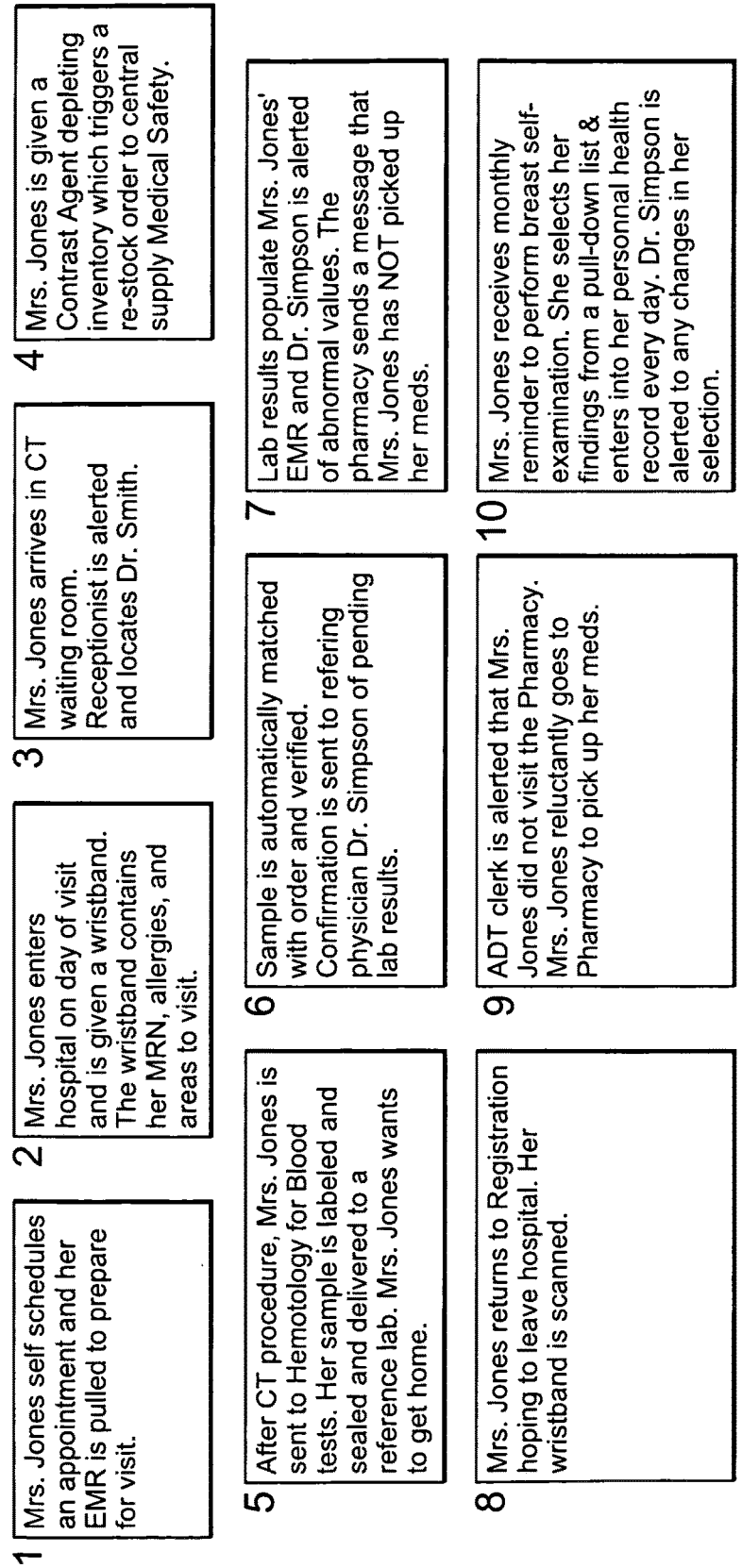

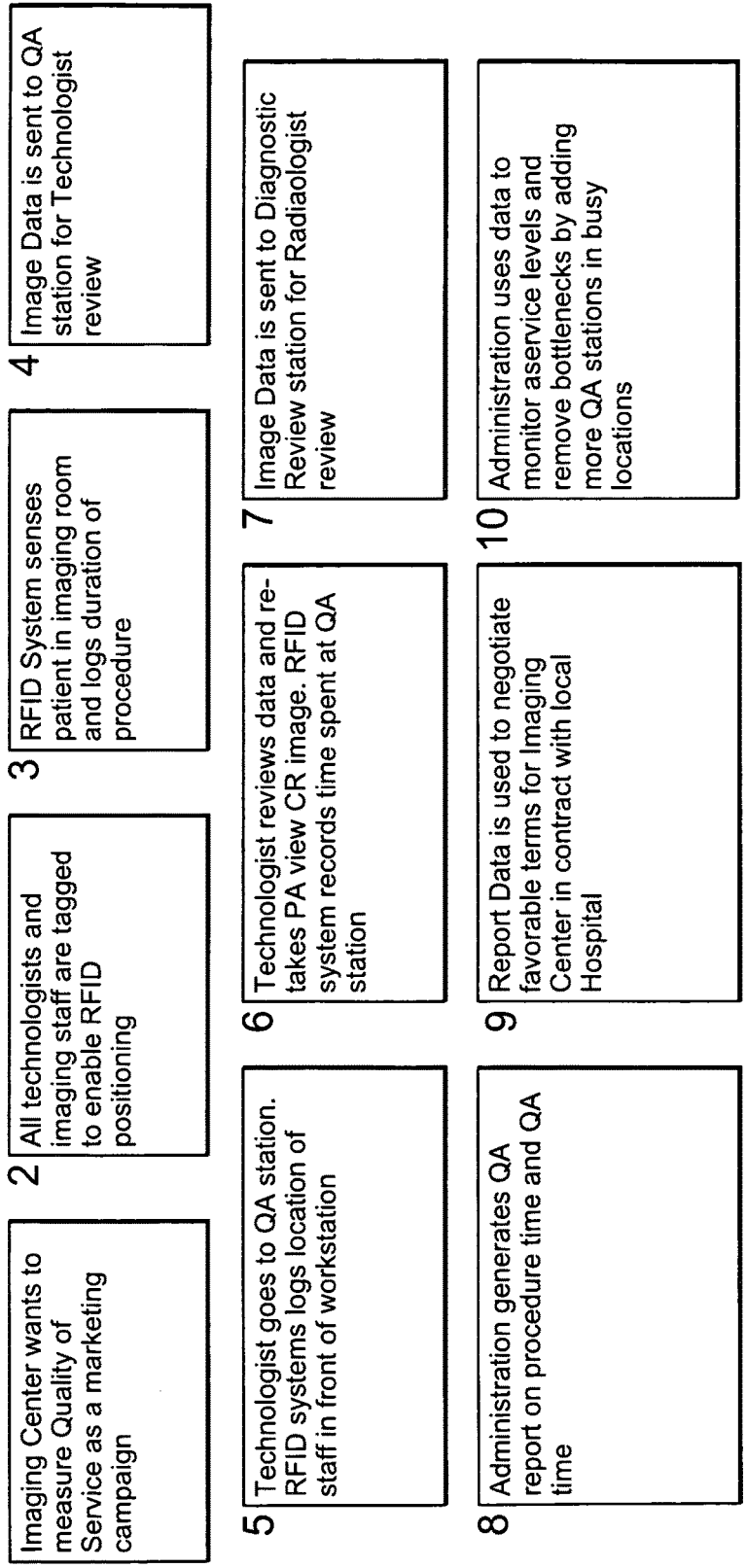

TAG BASED KNOWLEDGE SYSTEM FOR HEALTHCARE ENTERPRISES

This application claims priority to our U.S. provisional applications with the Ser. Nos. 60/791,058, filed Apr. 10, 2006, and 60/822,737, filed Aug. 17, 2006, both of which are incorporated by reference herein.

FIELD OF THE INVENTION

The field of the invention is data processing operations utilized in the practice, administration, or management of a healthcare enterprise (U.S. Class 705/28)

BACKGROUND

Healthcare enterprises, whether hospitals, nursing homes, surgical centers, physician's offices and so forth, all have challenges tracking their various assets. One problem is that such facilities typically contain a large number of different types of assets, including for example, rooms, gurneys, diagnostic equipment, treatment equipment, bandages and other supplies, drugs, and so forth. Another problem is that such assets are often mobile, and during the course of even a single day can be present at different times in a dozen or more different locations. Similar problems exist for personnel assets, including for example, physicians, nurses, technicians, and other personal.

In addition to difficulties in tracking assets, healthcare enterprises encounter significant difficulties in efficient utilization of assets. That situation occurs for numerous reasons, including for example the fact that many assets are only usable upon cleaning or other preparation, and many are suitable only in combination with other assets. Thus, an x-ray machine might only usable when there is a qualified x-ray technician available to operate it, and a physician might only be able to perform a surgical procedure when accompanied by a nurse having an appropriate skill set.

Healthcare enterprises have made considerable strides over the years in implementing computer systems that address materials management, bed management, staff timekeeping, pharmacy and lab procedures and reporting, and billing. Many enterprises have also implemented applications for specific departments, including for example the emergency rooms (ER), operating rooms (OR), intensive care unit (ICU), and cardiac care units (CCU). Unfortunately, many of these systems have trouble communicating with each other, and some do not communicate with other systems at all. Such lack of communication can significantly reduce efficiency and increase costs.

One might image that manufacturers of the existing systems would develop enterprise wide solution, and indeed in some instances that process is going forward. But enterprise-wide solutions run into enormous problems, not least because manufacturers commonly try to implement proprietary systems and methods that exclude their competitors, and that approach triggers enormous resistance from physicians and staff that might be force to adopt technologies with which they are unfamiliar or comfortable.

It is known that Radio Frequency Identification Tags (RFID tags) can be used to keep tabs on the locations of equipment, supplies, and so forth, and there are already systems on the market that utilize such information for specific applications. For example, there are RFID tag systems that are suitable for keeping track of locations of assets. In 2005 Cisco™ announced its Wireless Location Appliance™ 2700, which uses WiFi access points to gather signal strength indicators from 802.11 devices and tag, and triangulates the information to roughly determine the locations of the devices.

It is also known that RFID tags can be used to obtain and transmit physical parameters data (e.g., time, temp, and moisture, etc), and operational data (e.g., on/off, ready/not ready, damaged, being cleaned, etc). Several manufacturers have already announced plans to include such tags in their equipment, but there do not appear to be any such systems in common use. However, what does not seem to have been appreciated is that all three types of information described above as being derivable from RFID tags (location, physical parameters data, and operational data), can or should be combined and then distributed to multiple different computer systems in a healthcare environment.

It turns out that such a clearinghouse approach to RFID data can bring tremendous value in a highly cost-effective manner.

SUMMARY OF THE INVENTION

The present invention provides apparatus, systems, and methods in which RFID information is provided for multiple different purposes in a scalable, flexible manner, preferably using rules and correlations that can be altered by healthcare staff having little or no specialized information technology (IT) expertise. Such information may be further combined with patient telemetry to provide positional information of the patient and/or associated healthcare personnel.

The RFID information will typically include one or more of location information, physical parameters data, and operational data, and it is further contemplated that different types of items can be tagged, including equipment, people, and supplies. Any suitable type of tag, or combinations of different types of tags, can be utilized, with readers (also known as interrogators or transceivers) placed around the enterprise as appropriate. Contemplated systems can have anywhere from a single tag to 5,000 or even more tags in a large enterprise. The readers can advantageously be positioned such that at least 80% of the RFID information is refreshed at least every 10 minutes, and but more preferably the system would be implemented such that at least 80% of the RFID information is refreshed at least every minute.

The core of the system is contemplated to be embodied in a general purpose computer. Data entry and display devices communicatively coupled to the computer can be positioned throughout the enterprise, and can include electronic tablets, cell phones and pagers, as well as full sized data entry screens and displays such as might be found in accounting departments and nurses stations. In most or even all cases the data entry and display devices need not be dedicated to handling information derived from the RFID data. Preferred systems and methods include a Java or other cache that stores current RFID information, a rules based engine that derives events from the RFID information, a correlation engine that derives steps from the events, and an execution engine that delivers information relating to the steps. Ideally, staff members of the enterprise can define at least one of the rules and correlations entirely using menus and/or point and click techniques.

Events can fall within any appropriate range of generality to specialization. For example, an event might comprise "a doctor reported to the emergency room for duty" or "Dr. Jones reported to the emergency room for duty." The same is true of steps. One step might be to "discharge the patient" and another might be to "send an SMS message to Dr. Jones advising of delay in surgery." All realistic steps are contemplated, including one or more of sending a text message, a page or a voice message, and providing information to disparate systems, including a billing system, a bed management system, a staff timekeeping system, and a medical information system.

The inventive subject matter further provides systems, methods and devices in which are RFID circuitry is combined with a telemetry unit. The RFID circuitry can be combined with the telemetry unit in any suitable manner, including for example including the circuitry in a tag, and attaching the tag to the telemetry unit, or to a patient wearing the telemetry unit. The RFID circuitry preferably uses Ultra-Wide band frequency capability, or other high resolution technology. In especially preferred embodiments the RFID circuitry can provide resolution to below five feet in at least some area of a medical care facility that uses the telemetry unit.

In other contemplated uses, the RFID circuitry can be used to provide information used in billing use of the telemetry unit, or for some other aspect of billing. Additionally or alternatively, the RFID circuitry can provide information that is used to predict an event related to a patient carrying the telemetry unit and/or as input to an information technology software package in a medical care facility.

Various objects, features, aspects and advantages of the present invention will become more apparent from the following detailed description of preferred embodiments of the invention, along with the accompanying drawings in which like numerals represent like components.

BRIEF DESCRIPTION OF THE DRAWING

FIG. 3 is a high level flow chart of data flow within a preferred embodiment.

FIG. 4 is a chart showing sample records in a RFID table.

FIG. 5 is a chart showing sample records in a rules table.

FIG. 6 is a chart showing sample records in a correlations table.

FIGS. 7A and 7B are screen shots of portions of a floor map demonstrating zoom functionality on mobile assets.

FIG. 8 is a use case showing how patient care could be improved using a preferred embodiment.

FIG. 9 is a use case showing how operational efficiency could be improved using a preferred embodiment.

DETAILED DESCRIPTION

Figure 1:
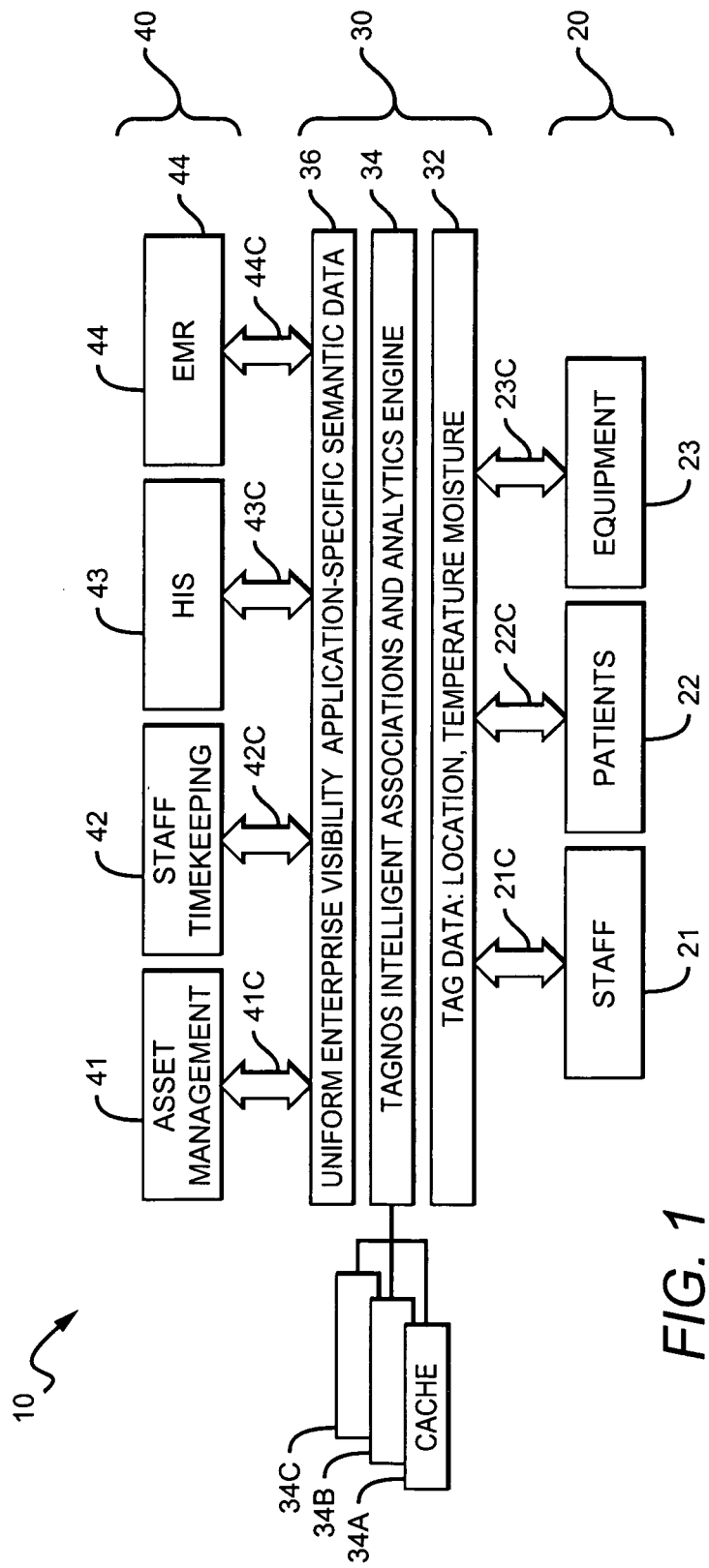
FIG. 1 is a conceptual diagram of an "Intelligent Clearing House" for RFID information.

FIG. 1 depicts an intelligent clearing house system 10 generally including RFID tagged items 20, computer processing hardware and software 30, and third party applications 40. Arrows 21C, 22C, 23C, 41C, 42C, 43C, and 44C depict communications to and from the computer processing hardware and software 30.

Tagged items 20 are shown in FIG. 1 as including Staff 21, Patients 22, and Equipment 23, but virtually anything can be tagged. One could, for example, tag consumables, and especially expensive or controlled substances such as certain drugs and stents. One could also tag documentation such as patient records, computer programs, computer printouts, journals and other library materials and periodicals.

In a real world implementation one would typically work backwards from a business problem being addressed. For example, if an enterprise is increasing capacity of an emergency room, it might be advisable to tag all the medical staff, the patients, and the medical equipment related to the ER. With staff one would typically include an RFID tag on the badges already used for identification, to access certain floors, or possibly on a radiation badge. One might also include a fingerprint or other biometric sensor. For patients it is most advantageous to tag the wrist or ankle bands, so that the tag remains with the patient throughout the stay. Alternatively or additionally, an enterprise could use a tag carried by a staff member or patient that is already included in his/her cell phone, pager, PDA or other device. One could put a patient tag on the patient's chart, but it is much better to put a patient tag on the patient and a document tag on the chart. Equipment is readily tagged directly on the unit, and in some cases the equipment might already by tagged.

It is contemplated that a single entity, whether staff, patient, equipment, or otherwise, could have any type of tag that is functional, and possibly multiple tags. The current preference appears to be for active tags, such as those available from Parco/Multispectral Solutions,™ Pango,™ Ekahau,™ Exavera,™ and Aeroscout™. Some active tags are disposable and some have replaceable batteries. Many modern active tags can operate on an ultra-wide band, and thereby have sufficiently low energy consumption to last four or more years on a single battery. Ultra-wide (UWB) frequency approved in June 2002 by the FCC for commercial use. UWB operates at a very high spectrum band (6.3 GHz) and therefore there are no interference and security issues. The nature of this frequency allows assets to be located within 1-foot granularity. The readers can see 600 feet and employ triangulation algorithms that eliminate the need to have readers in every room. These readers have low power needs and the batteries in the tags have a life of approximately 4 years. Currently preferred readers are those marketed by Parco and Multispectral.™

In general, the exact feature set of the tags is a matter of customer preference and need. Tags come in a variety of configurations, with the currently preferred tag being about 1 inch×1 inch (2.5 cm×2.5 cm) for equipment, a regular badge for staff, and a wristband for patients and visitors. Some installations prefer, or are already outfitted with, other types of tags such as passive, semi-passive, and/or semi-active tags. Some tags might deliver only identify information used for determining location, while other tags might provide other types of information such as physical parameters data (time, temperature, and moisture, etc) and operational data (e.g. on/off, status, etc).

A major strategic advantage in systems and methods described herein is that they can be completely hardware agnostic to the underlying RFID system that a particular prospective customer employs. Among other things this lowers the barrier to accepting the new service and facilitates choosing the best possible RFID hardware for a particular situation. As illustrated below, further benefits derive from employing a "command-center" approach that interfaces with different RF systems, and can become the central information processing unit of "who, what, where, and when" of medical equipment, staff and patients.

Any suitable type of tag, or combinations of different types of tags, can be utilized, provided appropriate readers are installed, and provided sufficient readers are placed around the enterprise. For example, if an enterprise uses ultra-wide band tags, then it needs to utilize at least some ultra-wide band readers. Contemplated systems can have anywhere from a single tag to 5,000 or even more tags in a large enterprise. The readers can advantageously be positioned such that at least 80% of the RFID information is refreshed at least every 10 minutes, and but more preferably the system would be implemented such that at least 80% of the RFID information is refreshed at least every minute. Typically one would place readers at doors to detect passive tags, and active tag readers on ceilings and hallways. Current active tag readers can often triangulate locations of tags from up to 200 meters away, through walls and other structures, with a resolution of only a meter or less.

Arrows 21C, 22C, and 23C represent potentially two-way communication between the tags and tagged items on the one hand, and the computer processing hardware and software 30 on the other hand. At the very least the tags need to wirelessly communicate with the tag readers (upward arrows), and the readers then typically communicate with the computer processing hardware and software 30 using cable or another wireless communication. The downward arrows typically depict communications to the tagged items rather than to the tag itself. For example, the computer processing hardware and software 30 might send an email, voice mail, or page to an appropriate device carried by a staff member or even a patient. It is contemplated that future tags will have displays associated with them, so that a lost patient, for example, could be located and directed back to his/her room.

Computer processing hardware and software 30 preferably contains at least the three layers shown. The lowest layer on the diagram is middleware 32, which receives tag data, such as location, duration, temperature, or moisture or other environmental parameters from the readers. Ideally, middleware 32 can be implemented in a generalized fashion to accommodate any needed inputs, thereby preventing the system from being tied to any particular manufacturer or model of tags or tag readers, or any particular telephone or other communications system. Having received the data, middleware 32 then preferably passes the data into the core engine, described here as an Intelligent Associations And Analytics Engine 34, which preferably has a hot cache or other memory structure 34A, 34B, and 34C and is preferably structured/operated under Java. The core engine 34 applies a set of rules to the RFID information to determine events, and applies correlations to the events to determine steps, and then executes or initiates execution of the steps. Some of those steps provide passing information along to the third party applications 40 via additional middleware 36, described here as the Uniform Enterprise Visibility Applications and Semantic Data. In real-world embodiments, middleware 36 is likely to be implemented as separate processors, such as the blades in a blade server, to handle communications with the various proprietary interfaces of the third party applications 40.

Arrows 41C, 42C, 43C and 44C represent communication between middle layer 36 and the third party applications 40. That communication will mostly involve one-way communication, with the middleware 36 supplying information to the third party applications 40 (upward arrows). But it is contemplated that one or more of the third party applications 40 could send inquiries or other data to the middleware 36 (downward arrows). Communication characterized by arrows 41C, 42C, 43C and 44D will likely, but not necessarily, be formatted according to a standard messaging protocol, such as Health Level 7, which is known in the art.

Hospitals can easily have dozens of third party applications, handling many different types of information. Among the contemplated third party applications are an asset management application 41, a staff timekeeping application 42, a hospital information application (HIS) 43, and an electronic medical records application 44. Another of the contemplated applications 40 is a web portal where hospital administrators can pull-up operational reports of not only their hospitals but, when appropriate, see similar reports on medical assets being used at other hospitals for the purpose of comparing notes and sharing and learning best practices. Currently this kind of information can only be obtained by one-to-one (versus many-to-many) conversations; poring through a vast array of industry publications; or by attending expensive, often distant, educational meetings. The web portal application highlights the healthcare IT industry's migration from providing pure information technology to providing information itself. Transcending conventional incremental benefits associated with the IT business, the addition of a rich and varied database of the latest information on products, services and methods employed by hospitals, is expected to empower hospital or other healthcare enterprise managers to perceive and react rapidly and in a manner adding significant value and cost savings to their organization. In essence, they will have this knowledge database to help them be proactive and either preclude or quickly "put out operational fires."

In yet another contemplated aspect, the "Intelligent Clearing House software" can have a mapper-software that integrates processed intelligent data to support Information Technology systems such as IDX, Cerner etc. inside the hospital through GUI screens and "point-and-click" software. Still further, an "Intelligent Clearing House software" engine can move beyond automatic detection of events to automated prediction of events. The predicted events could well comprise HL7 standard events, including for example patient admission, patient discharge, and so forth. Exemplary events include the following:

1) "Patient X-ray procedure complete": The system can detect that an X-ray procedure was completed, or that a surgical procedure is about to start, by determining that the patient was transported out of the X-ray room, waited in the radiology hallway for a bit, re-entered the X-ray room, and is just coming back to the surgical unit.

2) "Patient Transfer Complete": By detecting that a patient is transported from OR (after being in OR for 2 hours), and is the entering surgical unit, the system can determine that the patient left one unit of the hospital and is about to enter other.

3) "Equipment Sterilization Complete": By detecting that a equipment was moved to a sterilization unit, was in the sterilization room for a required number of minutes, the system can determine that the equipment is done with sterilization and is being moved back to a patient's room.

Figure 2:
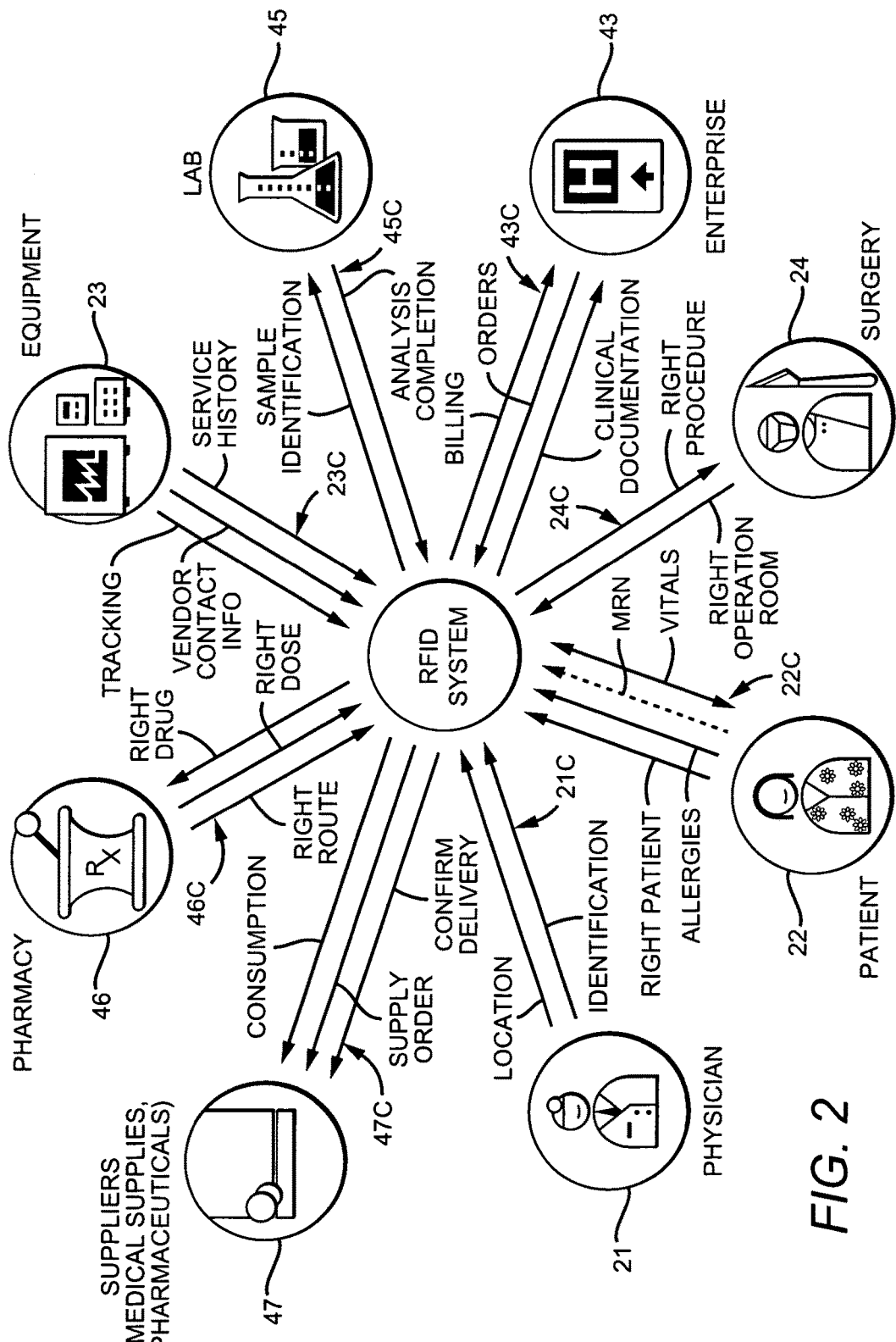
FIG. 2 is a conceptual diagram of an alternative view of the "Intelligent Clearing House" of FIG. 1.

FIG. 2 shows how implementations described herein can coordinate numerous aspects of information flow within a hospital or other health care enterprise, even though the subject matter is not directed to providing a completely unified system. In this instance there are icons for Physician (part of Staff 21), Patient 22, and Equipment 23, all in accordance with FIG. 1, and also additional icons for another type of tagged item (Surgery 24), and additional types of third party applications (Enterprise (HIS) 43, Lab 45, Pharmacy 46, and Suppliers 47). The central circle labeled "RFID System" corresponds to the computer processing hardware and software 30. Arrows 21C, 22C, 23C, and 43C correspond to the same numbered arrows in FIG. 1, while arrows 24C represent communication between tagged items in the operating room 24 (patient, staffs, or equipment) and middleware 32. Similarly, arrows 45C, 46C, and 47C represent communication between the third party applications in the lab 45, in pharmacy 46, and suppliers 47, respectively, and middleware 36.

In FIG. 3, the core engine 100 (34 of FIG. 1) applies a set of rules 112 to the RFID information 110 to determine events 120, applies correlations 122 to the events 120 to determine steps 130, and then executes 132 the steps 130. As described above, some of those steps 132 provide passing information along to the third party applications 40 via additional middleware 36. FIG. 4 depicts an exemplary portion of an RFID tag table, showing field designators (Tag ID, Tag Type, Tag Name, Coordinates, and Time Stamp) in the first column and four sample records in columns 2-5. The reader will note that FIGS. 4-6 are each oriented sideways to the normal viewing perspective; such that the columns represent individual records and the rows represent fields. FIG. 5 depicts an exemplary portion of an Event Rule table, showing field designators in the first column and four sample records in columns 2-5. Of course, it should be noted that the data can be generalized. Thus, the "who" field (row 4) could reference a type of asset and not necessarily an instance of the type. For example, the corresponding cell of record 1 might use the designation "Doctor" instead of including the literal "Dr. Jones", the corresponding cell. Similarly, the "where" could be "examining room" as opposed to a particular zone.

The data can also be used to interact with third party systems 40. For example, the message field (row 16) could be an HL7 communication to a third party application such as a bed management system, rather than a text message to the corresponding "who" field. Still further, the message could be a keystroke recording or other logon script, that accesses context relevant information (from one or more of the third party systems) with respect to the "who" or other information in record 1. FIG. 6 depicts a portion of a Correlation Engine table, showing field designators in the first column and four sample records in columns 2-5.

Figures 1, 7B:
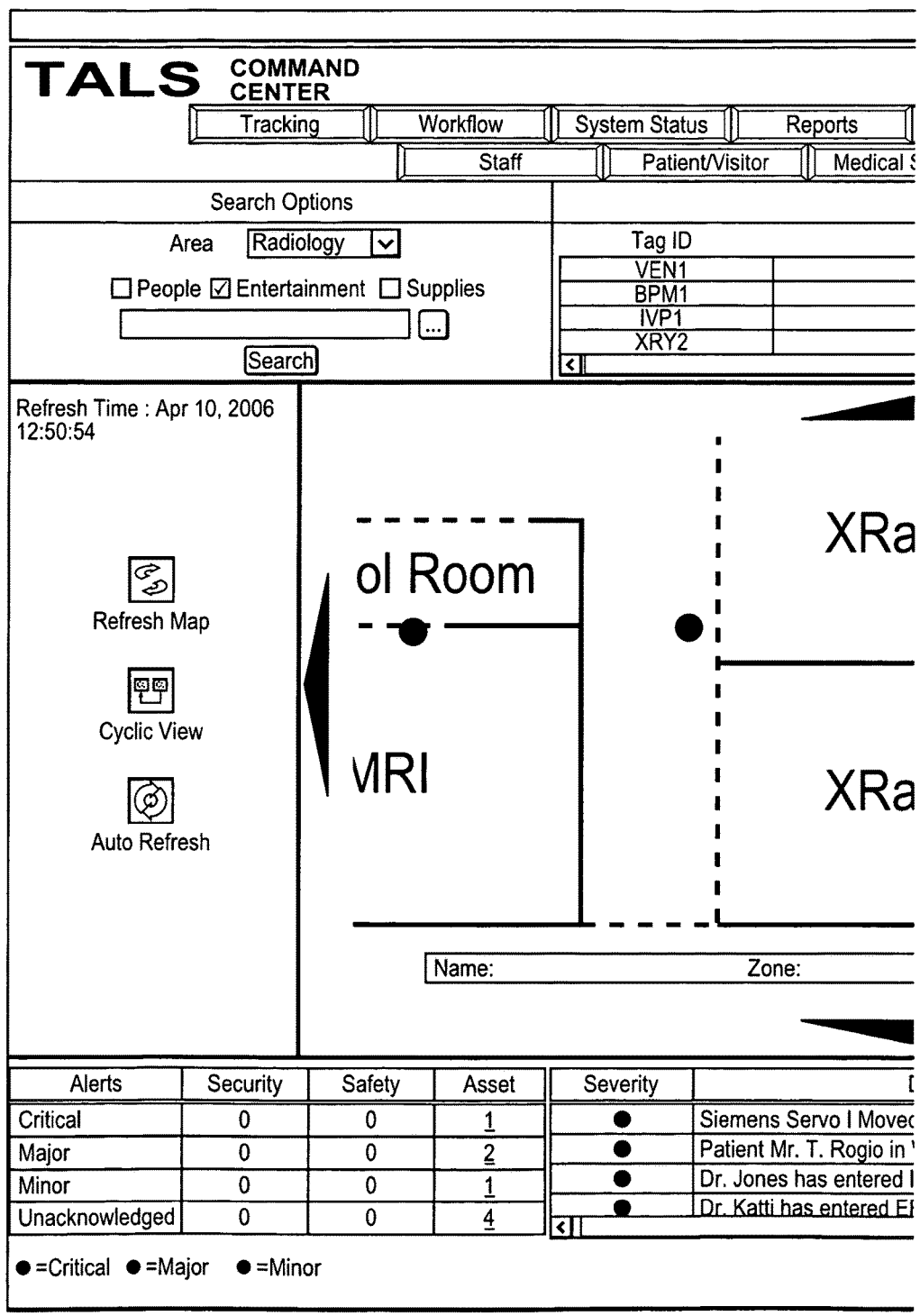

In terms of interfaces, several highly advantageous software functionalities are contemplated, including: (a) reporting the location of the responder as being within one of a plurality of business locations; (b) using scalar vector graphics to display the locations with varying degrees of detail (see FIGS. 7A and 7B); (c) displaying replay of movements of the assets; (d) displaying utilization profiles of the assets; and (e) coordinating the locations of the at least some of the assets data from a global satellite positioning system (GPS). It is still further contemplated that different ones of the readers (referenced earlier as responders) can operate with first and second different middleware, different frequencies, different types of interrogators, etc, and that the system according to the inventive subject matter can nevertheless consolidate output from the different types of equipment. This could be viewed as an "air-traffic controller" type of system, in that it can operate with and coordinate with a large number of different systems, some of which may be incompatible with each other. FIG. 8 is a use case showing how patient care could be improved using a preferred embodiment, and FIG. 9 is a use case showing how operational efficiency could be improved using a preferred embodiment.

Figure 10:
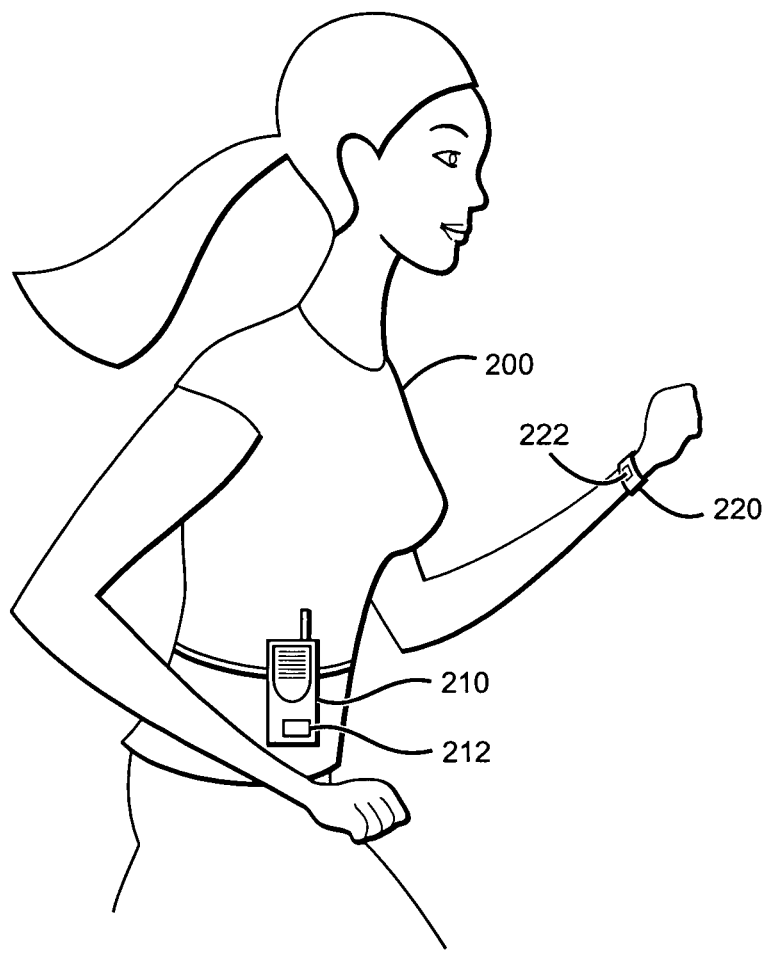
FIG. 10 is a perspective view of a person wearing a vital signs monitor box and a wristband, each tagged with an Ultra-Wide Band (UWB) Radio Frequency Identification (RFID) tag.

In yet another preferred aspect of the inventive subject matter as exemplarily depicted in FIG. 10, a person 200 is wearing a vital signs monitor device 210 tagged with a first Radio Frequency Identification (RFID) tag 212, and a patient identification wrist band 220 tagged with a second RFID tag 222. Of course, the person 210 shown is emblematic of all possible persons, regardless of gender, race, age, ambulatory status, and so forth.

The specific vital signs monitor device 210 shown here is a Micropaq™ device available from Welch Allyn™. Device 210, however, should be viewed as emblematic of all possible devices, including for example patient telemetry devices that might be larger or smaller, of different configurations, and regardless of how they are worn about the body. Many other devices that can serve the role of device 210 are known in the art. Thus, FIG. 10 should be interpreted broadly to include teachings and suggestions that the same, or an alternative, device could be worn about the chest, leg, coupled to a gurney carrying the person as a patient, and so forth. The critical limitations are that the device 210 can be carried on the person, has a portable power supply, has wireless communication capability, and monitors and provides data for at least one vital sign.

Similarly, the various tags 212, 222 should also be viewed from the broadest possible perspective, and are emblematic of all sizes and shapes of RFID tags, and all types of such tags including, for example, active or passive tags, standard or Ultra-Wide Band (UWB) frequency tags, and so on. There is, however, a definite preference for tags that can provide two dimensional spatial resolution in at least some portions of a typical hospital setting down to at least about 10 feet (3 meters), more preferably to at least two feet, and most preferably down to at least one foot resolution.

Adding a high-resolution RFID tag of whatever type to ISM and WMTS Wireless Telemetry band equipment is contemplated to be valuable in that it enables locating patients in substantially real-time with high resolution. This can be extremely useful, for example, in locating a patient when there is a "code-blue" situation, and also in locating nearby personnel and equipment when such tags are there as well. It is still further contemplated that use of high resolution RFID tags on patients (and/or on or in telemetry devices), in conjunction with appropriate software, can even identify when a patient falls to the floor, or for some other reason stops moving. In such case, an intelligent software system can dispatch nearest staff member. Yet another aspect of using UWB or other RFID tags on telemetry devices is that such use can facilitate efficient and accurate capture of billing information. Among other things the use of the device can be detected and charged on a per-day or other time basis.

In a still further aspect of contemplated systems and methods, inappropriate use of tagged patients can be reduced or at least documented. For example, nurses are expected to read a bar-code by scanning a patient wristband, and then to scan the bar-code on drug or medical supply being administered. Unfortunately, for convenience or other reasons, the patient wristband can be easily duplicated and scanned together with the drug or medical at the nurse's station, thus defeating an otherwise helpful safety system.

In contrast, contemplated systems using RFID technology are expected to improve patient identification accuracy. Active tags are being adopted to track patients, medical staff, and medical equipment. But due to economical reasons, the drugs, medical supplies and lab specimens will continue to have bar-coding or passive tags which will need some type of handheld reader and manual intervention to read. Consequently, it is contemplated that the handheld reader to read bar-code or passive tag on drug, medical supply or lab specimen also includes an active tag embedded or slapped-on, which will help to close the loop on complete matching of "five rights" before the patient is delivered some type of clinical service (The physical location of this hand-held reader that is scanning the drug, medical supply, lab specimen will ensure physical proximity check to the patient automatically). In such case, when the clinician comes closer to the patient, and both are wearing active tags, the identification of the patient is automatically done through proximity. The next step is for the clinician to actually administer a drug, use some medical supply, verify a specimen or perform some procedure. It should be appreciated that RFID tags cannot be easily duplicated or printed like barcodes. There is also no ability to verify where the patient bar-code wristband is being read. In the above method, the physical location of the patient is known as well as the location of medical staff and the hand-held reader that is reading the drug, medical supply or lab specimen, which helps enforcing the "five rights" check with automation using new type hand-held reader and a new method.

Consequently, it is particularly contemplated that conventional handheld readers are used to scan a barcode or passive tag (e.g., on a drug, medical supply, lab specimen etc.) and that such devices are coupled to an active, semi-active or even passive RFID tag with any radio frequency (HF, UHF, 2.4 GHz, 6.3 GHz and so on) or any wireless standard (Wi-fi, Zigbee, UWB and so on). Most preferably, such tagged readers are then used in the context of FIGS. 1 and/or 2.

It should be noted that implementations according to the inventive subject matter presented herein offer many benefits. Among other advantages, intelligent RFID technology provides healthcare providers a dynamic and visual model on patient flow at the facility, giving insight on efficiency and quantity of asset usage. Users can instantly locate assets like medical staff, medical equipment, medical supplies, and patients, offering total asset visibility to the healthcare organization. The Return-on-Investment (ROI) is supported by more accurate patient billing, better asset utilization, and better asset preventive maintenance, reduced asset shrinkage, better security, increased productivity, reduced medical errors, thus reducing costs and increasing quality of care and safety. Intelligent asset utilization increases tend to reduce asset purchases and rental bills, an increase in equipment billing accuracies (and in future versions even tagged drugs and medical supplies), cuts asset shrinkage, and potentially increased facility throughput due to increased productivity.

Currently, hospitals are focusing their RFID adoption activities on medical equipment tagging for the purpose of gaining operational insights about equipment utilization, maintenance and billing. But the benefits become even greater as RFID tags become more intelligent and go beyond simple locating functions, e.g., to sense temperature, moisture etc. Among other things the systems and methods described herein provide powerful processing software to harvest all of a client's incremental data as it flows in and through the organization, leading to improved staff productivity (e.g., by finding equipment, staff, and patients easily), which results in reductions in wasted manpower time and effort. Systems and methods according to the inventive subject matter will also reduce patient stays inside hospitals while increasing quality-of-care (e.g., by being able to track and treat patients and monitor their care and medications more efficiently).

Viewed from a difference perspective, contemplated systems and methods may be viewed as adding a horizontal "layer" that cuts across multiple (often disparate) IT systems; each handling a specific vertical operation like asset management, staff time keeping, EMR (Electronic Medical Record), HIS (Hospital Information System), and PhIS (Pharmacy Information System). In effect, these systems and methods permit creation of an "Intranet" connecting medical staff, patients and equipment into an automated and coherent universal communication and real-time operational analysis platform.

Thus, specific embodiments and applications of systems and methods for tag based knowledge systems for healthcare enterprises have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A method for deploying an automated scheduling system within a healthcare enterprise, the automated scheduling system running on a computer processing unit that includes hardware and software, the method comprising:
    tagging a patient with a first RFID tag;
    tagging a healthcare asset with a second RFID tag; affixing more than one RFID tag to the healthcare asset;
    placing a plurality of RFID readers within the enterprise, the readers configured to cooperate (a) with the first RFID tag to send to the scheduling system location and identification information of the patient, and (b) with the second RFID tag to send to the scheduling system location and identification information of the healthcare asset;
    submitting a first rule to the automated scheduling system configured to cause the computer processing unit to automatically send a first electronic message to a first staff member based upon the location and identification information of the patient; and
    correlating a physical proximity of the first and second tags as an antecedent step to delivering a clinical service to the patient;
    wherein the first staff member is not the healthcare asset;
    wherein the first RFID tag further comprises at least one of an Ultra-Wide band and Ultrasound frequency capability.

2. The method of claim 1, further comprising tagging at least one of an electronic device, a staff member, a mechanical device, or another patient with an RFID tag.

3. The method of claim 1, wherein the first RFID tag is a different type of tag than the second RFID tag.

4. The method of claim 1, wherein the information sent to the scheduling system further comprises physical parameters data selected from the group consisting of an environmental parameter and time.

5. The method of claim 1, wherein the information sent to the scheduling system further comprises operational data selected from the group consisting of on/off status, functional status, maintenance status, analytic data of a clinical test, and a replenishment trigger signal.

6. The method of claim 1, wherein at least 80% of the information sent to the scheduling system is refreshed at least every 10 minutes.

7. The method of claim 1, wherein the first electronic message comprises a first procedural step.

8. The method of claim 1, wherein the healthcare asset is one of a medical care provider, a medical equipment, a drug, or a document.

9. The method of claim 1, wherein the healthcare asset is a combination of more than one of a medical care provider, a medical equipment, a drug, or a document.

10. The method of claim 1, wherein the computer processing unit sends the first electronic message to more than one staff member.

11. The method of claim 1, wherein the computer processing unit sends the first electronic message to the first staff member and a second electronic message to a second staff member.

12. The method of claim 1, wherein the clinical service is at least one of administering a drug, using a medical supply, verifying a specimen, or performing a procedure.

13. The method of claim 1, wherein more than one procedural step is associated with the first electronic message.

14. The method of claim 1, wherein the first rule triggers the first electronic message and a second rule triggers a second electronic message.

15. The method of claim 1, further comprising the computer processing unit sending a second electronic message to one of at least a second staff member, a computer system, an automated machine, or a communication system.

16. The method of claim 1, wherein the electronic message comprises a billing data for the patient.

17. The method of claim 1, wherein the first electronic message comprises the location information of the healthcare asset.

18. The method of claim 1, further comprising the computer processing unit sending a second electronic message comprising a set of staffing attributes to a staff timekeeping system.

19. The method of claim 1, wherein the first electronic message instructs the first staff member to use a piece of equipment to perform a procedural step.

20. The method of claim 8, wherein the first procedural step comprises retrieving the healthcare asset.

21. The method of claim 1, further comprising tagging the staff member with a third RFID tag.

22. The method of claim 1, wherein the healthcare asset comprises a medical information regarding the patient.

23. The method of claim 22, wherein the medical information is selected from the list consisting of a medical history, a diagnosis, a drug listing, a radiographic image, and a healthcare plan information.

24. The method of claim 1, further comprising associating a positional attribute with the second RFID tag by combining a telemetry unit with the second RFID tag.

25. The method of claim 1, wherein at least one of the plurality of RFID readers has a resolution less than five feet.

26. The method of claim 1, wherein the plurality of RFID readers has a resolution below five feet.

27. The method of claim 1, wherein the plurality of RFID readers are accurate to at least one of a room, a sub-room, or a bed level.

28. The method of claim 1, further comprising displaying the first electronic message on a handheld device.

29. An automated scheduling system in a healthcare enterprise, comprising:
an RFID receiver configured to receive:
a first set of RFID information from a first RFID tag, the first set of RFID information including a first location attribute and a first identification attribute, wherein the first RFID tag is tagged to a patient; and
a second set of RFID information from a second RFID tag, the second set of RFID information including a second location attribute and a second identification attribute, wherein the second RFID tag is tagged to a healthcare asset; wherein the first RFID tag is a different type of tag than the second RFID tag;
a computer processing unit that includes hardware and software, communicatively coupled to the RFID receiver;
wherein the computer processing unit is configured to:
receive a rule, wherein the rule is entered via a user interface; wherein the user interface is configured to allow a user to select the rule via graphical menus; and
associate the first location attribute and the first identification attribute with a first message based on the rule;
send the first message to a first staff member based upon the rule and the first and second sets of RFID information; and
wherein correlating a physical proximity of the first and second tags by the system is an antecedent step to delivering a clinical service to the patient.

30. The system of claim 29, further comprising tagging at least one of an electronic device, a staff member, a mechanical device, or another patient with an RFID tag.

31. The system of claim 29, wherein the first set of RFID information includes physical parameters data selected from the group consisting of an environmental parameter and time.

32. The system of claim 29, wherein a portion of the first set of RFID information is the same as a portion of the second set of RFID information.

33. The system of claim 29, wherein the first message comprises a first procedural step.

34. The system of claim 29, wherein the first RFID tag further comprises at least one of an Ultra-Wide band and Ultrasound frequency capability.

35. The system of claim 29, wherein the first message is sent to more than one staff member.

36. The system of claim 29, wherein the healthcare asset is one of a medical care provider, a medical equipment, a drug, or a document.

37. The system of claim 29, wherein more than one message is sent to more than one staff member.

38. The system of claim 29, wherein the first message instructs the first staff member to perform a first procedural step, and a second message instructs a second staff member to perform a second procedural step.

39. The method of claim 29, wherein the healthcare asset is a combination of more than one of a medical care provider, a medical equipment, a drug, or a document.

40. The system of claim 29, wherein the computer processing unit sends more than one message based upon the rule and the first and second sets of RFID information.

41. The system of claim 29, wherein a second message is sent to a computer system to execute a first procedural step.

* * * * *